US012781192B2

(12) United States Patent
Matsusaki et al.

(10) Patent No.: US 12,781,192 B2
(45) Date of Patent: Nov. 3, 2026

(54) METHOD FOR PRODUCING TISSUE BODY AND METHOD FOR PROMOTING DIFFERENTIATION OF FAT-DERIVED STEM CELLS

(71) Applicants: TOPPAN Holdings Inc., Tokyo (JP); The University of Osaka, Suita (JP)

(72) Inventors: Michiya Matsusaki, Suita (JP); Fiona Louis, Suita (FR); Shiro Kitano, Tokyo (JP)

(73) Assignees: TOPPAN Holdings Inc., Tokyo (JP); The University of Osaka, Osaka (JP)

( * ) Notice: Subject to any disclaimer, the term of this patent is extended or adjusted under 35 U.S.C. 154(b) by 467 days.

(21) Appl. No.: 18/253,460

(22) PCT Filed: Oct. 8, 2021

(86) PCT No.: PCT/JP2021/037368
§ 371 (c)(1),
(2) Date: May 18, 2023

(87) PCT Pub. No.: WO2022/113540
PCT Pub. Date: Jun. 2, 2022

(65) Prior Publication Data
US 2025/0320464 A1 Oct. 16, 2025

(30) Foreign Application Priority Data
Nov. 26, 2020 (JP) ................................ 2020-196209

(51) Int. Cl.
*C12N 5/0775* (2010.01)
*C12N 5/00* (2006.01)
*C12N 5/071* (2010.01)

(52) U.S. Cl.
CPC ........... *C12N 5/069* (2013.01); *C12N 5/0062* (2013.01); *C12N 5/0667* (2013.01); *C12N 2502/1382* (2013.01); *C12N 2506/1384* (2013.01); *C12N 2513/00* (2013.01); *C12N 2533/54* (2013.01)

(58) Field of Classification Search
None
See application file for complete search history.

(56) References Cited

U.S. PATENT DOCUMENTS

2014/0206029 A1 7/2014 Aalto-Setälä

FOREIGN PATENT DOCUMENTS

WO WO 2015/072164 A1 5/2015
WO WO 2017/146124 A1 8/2017
WO WO 2018/143286 A1 8/2018
WO WO 2020/203369 A1 10/2020

OTHER PUBLICATIONS

WIPO English Machine Translation of WO 2020/203369, published Oct. 8, 2020 (Year: 2020).*
Abbas Heidari-Moghadam et al., "Role of Vascular Endothelial Growth Factor and Human Umbilical Vein Endothelial Cells in Designing An In Vitro Vascular-Muscle Cellular Model Using Adipose-Derived Stem Cells", Cell J, July 2020. vol. 22, p. 19-p. 28*.
Soo-Eun Sung et al., "MyoD Overexpressed Equine Adipose-Derived Stem Cells Enhanced Myogenic Differentiation Potential", Cell Transplant, 2016. vol. 25, p. 2017-p. 2026*.
Taofeng Lu et al, "Isolation and Characterization of Adipose-derived Mesenchymal Stem Cells (ADSCS) from Cattle", Appl. Biochem.Biotechnol, 2014. vol. 174, p. 719-p. 728*.
International Search Report (PCT/ISA/210) for International Application No. PCT/JP2021/037368 dated Nov. 30, 2021.
English Translation of IPRP (PCT/IB/338 and PCT/IB/373) (Jun. 8, 2023 and May 30, 2023) and the Written Opinion of ISA (PCT/ISA/237) issued in International Application No. PCT/JP2021/037368 dated Nov. 30, 2021 (6 pages).
Lidong Guan et al, "In vitro differentiation of human adipose-derived mesenchymal stem cells into endothelial-like cells", Chinese Science Bulletin, Science in China Press, BE, vol. 51, No. 15, Aug. 1, 2006, p. 1863-p. 1868, XP019438569*.
Kang Dong-Hee et al, "Engineered Whole Cut Meats Assembled of Cell Fibers Constructed by Tendon-Gel Integrated Bioprinting", Research Square, Oct. 13, 2020, XP055970022*.
Extended European Search Report issued in counterpart European Application No. 21897518.3 dated Feb. 13, 2024.
Dong-Hee Kang, "Engineered whole cut meat-like tissue by the assembly of cell fibers using tendon-gel integrated bioprinting", Nature Communications | https://doi.org/10.1038/s41467-021-25236-9, 12pp.
Chinese Office Action issued Jul. 18, 2026, in Chinese Patent Application No. 202180071450.8, 37pp.

* cited by examiner

*Primary Examiner* — Evelyn Y Pyla
(74) *Attorney, Agent, or Firm* — XSENSUS LLP

(57) ABSTRACT

Disclosed is a method for producing a tissue construct comprising vascular cells, comprising incubating cells comprising at least fat-derived stem cells in the presence of horse serum.

9 Claims, 7 Drawing Sheets

METHOD FOR PRODUCING TISSUE BODY AND METHOD FOR PROMOTING DIFFERENTIATION OF FAT-DERIVED STEM CELLS

CROSS REFERENCE TO RELATED APPLICATIONS

This application is a 35 USC 371 U.S. national stage application of International Application No. PCT/JP2021/037368, filed on Oct. 8, 2021, which claims the priority benefit to Japanese Application No. 2020-196209, filed on Nov. 26, 2020. The International Application and the Japanese Application are incorporated by reference herein in their entirety.

TECHNICAL FIELD

The present invention relates to a method for producing a tissue construct, and a method for promoting the differentiation of fat-derived stem cells.

BACKGROUND ART

Known as techniques to artificially produce constructs simulating biological tissues are, for example, a method of producing a three-dimensional tissue construct, the method including three-dimensionally disposing cells each coated with a coating film containing collagen to form a three-dimensional tissue construct (Patent Literature 1), and a method of producing a three-dimensional cellular tissue, the method including: mixing cells with a cationic substance and an extracellular matrix component to give a mixture; collecting cells from the resulting mixture; and forming a cell aggregate on a substrate (Patent Literature 2). The present inventors have proposed a method for producing a large-sized three-dimensional tissue construct having a thickness of 1 mm or more with use of a relatively small number of cells by bringing cells and fragmented exogenous collagen into contact with each other (Patent Literature 3).

CITATION LIST

Patent Literature

Patent Literature 1: International Publication No. WO 2015/072164
Patent Literature 2: International Publication No. WO 2017/146124
Patent Literature 3: International Publication No. WO 2018/143286

SUMMARY OF INVENTION

Technical Problem

Three-dimensional tissue constructs, which are aggregates of cells artificially produced by cell culture, can be obtained according to any of the above-mentioned production methods. In particular, three-dimensional tissue constructs comprising vascular cells are expected to be used as alternatives for experimental animals, materials for transplantation, and so on, for example, from the viewpoints of maintenance of three-dimensional tissue constructs and engraftment in being transplanted, and a method for promoting the differentiation of fat-derived stem cells into vascular cells is demanded for producing three-dimensional tissue constructs comprising vascular cells.

The present invention was made in view of the above circumstance, and an object of the present invention is to provide a method for promoting the differentiation of fat-derived stem cells into vascular cells in producing tissue constructs comprising vascular cells.

Solution to Problem

The present inventors diligently studied to find that the differentiation of fat-derived stem cells into vascular cells is promoted by incubating fat-derived stem cells in the presence of horse serum, which led to the completion of the present invention.

Specifically, the present invention includes, for example, the followings.

[1] A method for producing a tissue construct comprising vascular cells, comprising incubating cells comprising at least fat-derived stem cells in the presence of horse serum.

[2] The method of [1], wherein the tissue construct comprising vascular cells includes a vascular network.

[3] The method of [1] or [2], wherein the cells comprising at least fat-derived stem cells include no vascular cell.

[4] The method of any one of [1] to [3], wherein the incubating in the presence of horse serum is incubating in a culture medium comprising the horse serum.

[5] The method of any one of [1] to [4], wherein the fat-derived stem cells are bovine-derived.

[6] The method of any one of [1] to [5], wherein the incubating is performed for 144 hours or more.

[7] The method of any one of [1] to [6], comprising incubating cells comprising at least fat-derived stem cells together with a fragmented extracellular matrix component in the presence of horse serum.

[8] The method of [7], wherein the fragmented extracellular matrix component is disposed in a gap among the cells in the tissue construct comprising vascular cells.

[9] The method of [7] or [8], wherein the fragmented extracellular matrix component is a fragmented collagen component.

[10] The method of any one of [7] to [9], comprising:

a step of bringing the cells into contact with the fragmented extracellular matrix component in an aqueous medium before incubation, wherein the incubating cells comprising at least fat-derived stem cells in the presence of horse serum is a step of incubating the cells brought into contact with the fragmented extracellular matrix component in the presence of horse serum, and the tissue construct comprising vascular cells is a three-dimensional tissue construct comprising vascular cells.

[11] A method for promoting differentiation of fat-derived stem cells, comprising incubating cells comprising at least fat-derived stem cells in the presence of horse serum.

[12] The method of [11], wherein the incubating in the presence of horse serum is incubating in a culture medium comprising the horse serum.

[13] The method of or [12], wherein the fat-derived stem cells are bovine-derived.

[14] The method of any one of to [13], wherein the incubating is performed for 144 hours or more.

[15] The method of any one of to [14], comprising:

incubating cells comprising at least fat-derived stem cells and a fragmented extracellular matrix component in the presence of horse serum.

[16] The method of [15], wherein the fragmented extracellular matrix component is a fragmented collagen component.

Advantageous Effect of Invention

According to the present invention, the differentiation of fat-derived stem cells into vascular cells is promoted. Tissue constructs comprising vascular cells can be produced in a short time by promoting the differentiation into vascular cells.

DESCRIPTION OF EMBODIMENTS

Figure 1:
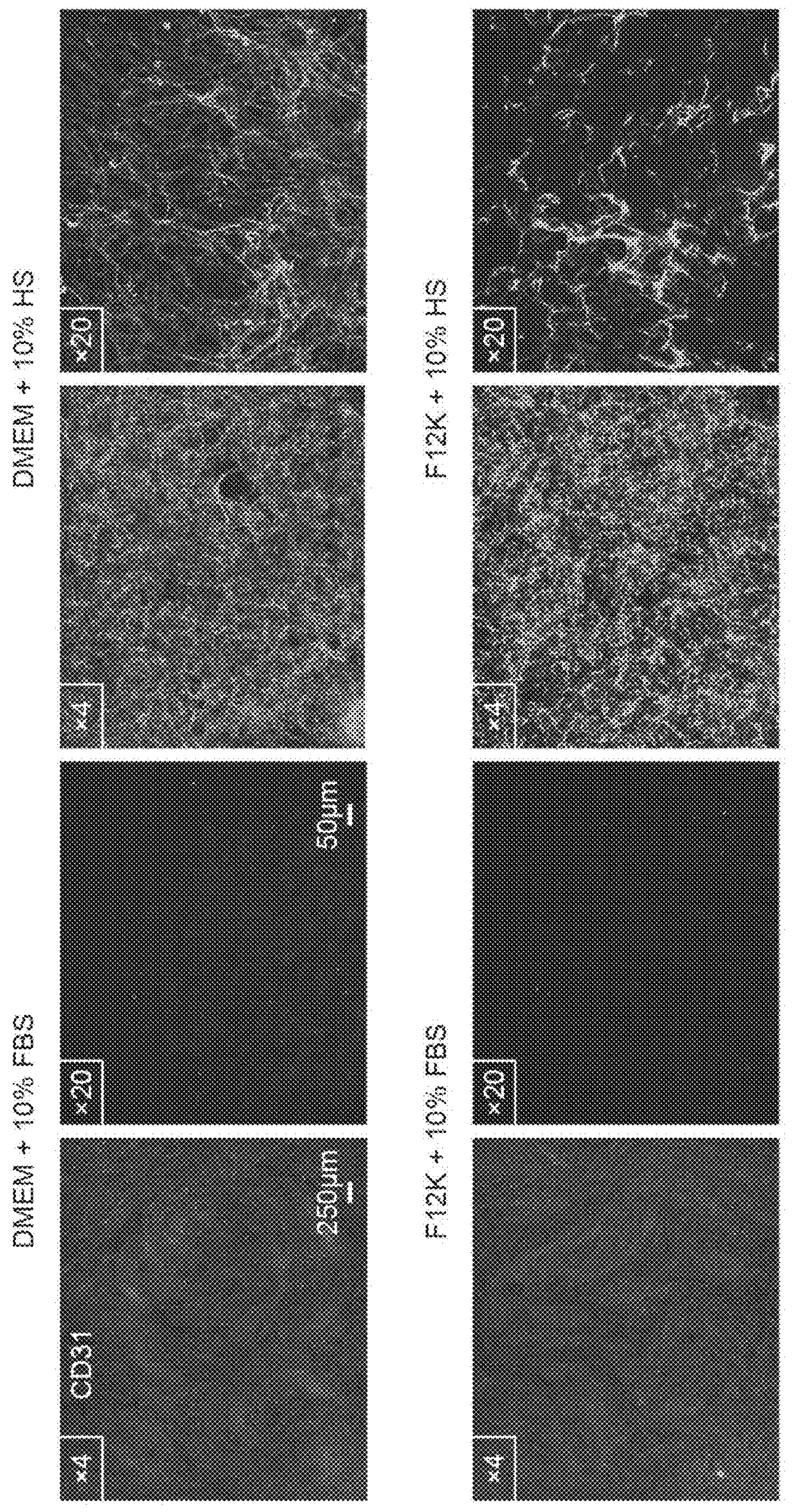
FIG. 1 shows results of CD31 immunostaining for tissues produced in Production Example 1.

Hereinafter, modes for implementing the present invention will be described in detail. However, the present invention is not limited to the following embodiments.

The present invention provides, as an embodiment, a method for producing a tissue construct comprising vascular cells, comprising incubating cells comprising at least fat-derived stem cells in the presence of horse serum.

Herein, the "tissue construct" refers to a tissue including cells that is artificially made by cell culture. The "tissue construct" may be a "two-dimensional tissue construct" in which cells are two-dimensionally disposed, or a "three-dimensional tissue construct" as an aggregate of cells (aggregated cell population) in which cells are three-dimensionally disposed. The two-dimensional tissue construct is a construct obtained by culturing cells planarly, and present, for example, in such a shape that cells are extended planarly on a substrate. If the three-dimensional tissue construct includes an extracellular matrix component described later, cells are three-dimensionally disposed via the extracellular matrix component. The shape of the three-dimensional tissue construct is not limited in any way, and examples thereof include sheet-like, spherical, generally spherical, ellipsoidal, generally ellipsoidal, hemispherical, generally hemispherical, semicircular, generally semicircular, cuboidal, and generally cuboidal shapes. Here, biological tissue constructs include sweat glands, lymphatic vessels, sebaceous glands, and so on, and their configurations are more complex than that of the three-dimensional tissue construct. Therefore, the three-dimensional tissue construct and biological tissues are readily distinguishable from each other.

Herein, the "cells" are not limited in any way, and may be cells derived from a mammal such as a human, a monkey, a dog, a cat, a rabbit, a pig, a bovine, a mouse, and a rat. The site from which the cells are derived is not limited in any way, too, and the cells may be somatic cells derived, for example, from the bone, muscle, internal organ, nerve, brain, bone, skin, or blood, or germ cells. Further, the cells may be stem cells, or cultured cells such as primary cultured cells, subcultured cells, and established cells.

Herein, the "stem cells" refer to cells possessing replication competence and pluripotency. Included in stem cells are pluripotent stem cells, which possess ability to differentiate into any type of cells, and tissue stem cells (also called somatic stem cells), which possess ability to differentiate into a particular type of cells. Examples of pluripotent stem cells include embryonic stem cells (ES cells), nuclear transfer embryonic stem cells (ntES cells), and induced pluripotent stem cells (iPS cells). Examples of tissue stem cells include mesenchymal stem cells (e.g., fat-derived stem cells, bone marrow-derived stem cells), hematopoietic stem cells, and neural stem cells. Examples of fat-derived stem cells (ADSCs) include human fat-derived stem cells and bovine fat-derived stem cells.

The cells at least include fat-derived stem cells. The origin of the fat-derived stem cells is not limited in any way, and stem cells collected, for example, from subcutaneous adipose tissue or epicardium-derived adipose tissue may be used. If a tissue construct (e.g., a three-dimensional tissue construct) comprising mature adipocytes, which is produced by the method of the present embodiment, is to be ultimately used to simulate tissue at a particular part in the living construct, it is preferable to use mature adipocytes derived from tissue corresponding to the tissue at the part. For the fat-derived stem cells, for example, bovine-derived, horse-derived, mouse-derived, rat-derived, pig-derived, or human-derived stem cells may be used. According to the method of the present embodiment, the differentiation into vascular cells can be promoted even by using bovine-derived fat-derived stem cells, which are known to be especially difficult to differentiate into vascular cells. Therefore, use of bovine-derived fat-derived stem cells is preferable because the advantageous effect of the present invention becomes more significant.

The cells may further include cells other than fat-derived stem cells. Examples of cells other than fat-derived stem cells include mesenchymal cells such as vascular endothelial cells, adipocytes, fibroblasts, chondrocytes, and osteoblasts, cancer cells such as large bowel cancer cells (e.g., human large bowel cancer cells (HT29)) and liver cancer cells, cardiomyocytes, epithelial cells (e.g., human gingival epithelial cells), lymphatic endothelial cells, neurons, dendritic cells, hepatocytes, adherent cells (e.g., immunocytes), smooth muscle cells (e.g., aortic smooth muscle cells (Aorta-SMCs)), pancreatic islet cells, and keratinocytes (e.g., human epidermal keratinocytes). Herein, the "adipocytes" refer to all types of adipocytes except fat-derived stem cells, and include mature adipocytes and adipocytes not falling within fat-derived stem cells.

However, it is preferable for exerting the effect of promoting the differentiation of fat-derived stem cells into mature adipocytes in the present invention that the cells comprising at least fat-derived stem cells, that is, the cells before incubation include no vascular cell because the advantageous effect of the present invention becomes more significant.

It is preferable that 90% or more of the total cell count of the cells before incubation be fat-derived stem cells, and it is more preferable that all the cells before incubation be fat-derived stem cells.

The cells may further include vascular endothelial cells. Herein, "vascular endothelial cells" refer to flat cells constituting the surface of the intravascular space. Examples of the vascular endothelial cells include human umbilical vein endothelial cells (HUVECs).

The size of a lipid droplet can be used as an index indicating the degree of maturity of an adipocyte. The lipid droplet is an intracellular organelle that stores lipids such as triglyceride (neutral fat) and cholesterol, and has a droplet-like shape with the lipids covered by a monolayer of phospholipid. Expression of a protein unique to adipose tissue (e.g., perilipin) is found on the surface of the phospholipid. The size of the lipid droplet varies among adipocytes that have matured, and if the average value of the size of the lipid droplet is 20 μm or more, for example, the adipocytes can be regarded to have matured to some degree, that is, can be regarded as mature adipocytes.

The tissue construct at least includes vascular cells. For example, vascular endothelial cells are included in the vascular cells. Herein, "vascular endothelial cells" refer to flat cells constituting the surface of the intravascular space.

The content of the vascular cells in the tissue construct to the total cell count in the tissue construct may be, for example, 5% or more, 10% or more, 15% or more, 20% or more, 25% or more, or 30% or more, and may be 95% or less, 90% or less, 80% or less, or 75% or less.

If the tissue construct includes vascular endothelial cells, the content of the vascular endothelial cells to the total cell count in the tissue construct may be, for example, 5% or more, 10% or more, 15% or more, 20% or more, 25% or more, or 30% or more, and may be 95% or less, 90% or less, 80% or less, or 75% or less.

The tissue construct may further include cells other than vascular cells. Examples of the cells other than vascular cells include mesenchymal cells such as fibroblasts, chondrocytes, and osteoblasts, cancer cells such as large bowel cancer cells (e.g., human large bowel cancer cells (HT29)) and liver cancer cells, cardiomyocytes, epithelial cells (e.g., human gingival epithelial cells), lymphatic endothelial cells, neurons, dendritic cells, hepatocytes, adherent cells (e.g., immunocytes), smooth muscle cells (e.g., aortic smooth muscle cells (Aorta-SMCs)), pancreatic islet cells, and keratinocytes (e.g., human epidermal keratinocytes). However, it is preferable for exerting the effect of promoting the differentiation of fat-derived stem cells into vascular cells in the present invention that 10% or less of the total cell count in the tissue construct after incubation described later be fat-derived stem cells, it is more preferable that 5% or less of the total cell count in the tissue construct after incubation be fat-derived stem cells, and it is even more preferable that the tissue construct include no fat-derived stem cell, because the advantageous effect of the present invention becomes more significant.

The tissue construct may include an intercellular vascular network. If an intercellular vascular network is formed, the tissue construct is expected to be successfully maintained for a long period of time, and the tissue construct is expected to be readily engrafted in being transplanted into mammals and so on.

"Comprising an intercellular vascular network" means comprising a structure in which branched blood vessels extend among cells to surround the cells like biological tissues. Whether a vascular network like those of biological tissues is formed can be determined, for example, on the basis of the number of vascular branches and/or the vascular interbranch lengths and/or the diversity of vascular diameter in biological tissues. If the average value of the number of vascular branches in the tissue construct to the average value of the number of vascular branches in biological tissues is 80% or more and 150% or less, 85% or more and 130% or less, or 90% or more and 120% or less, for example, the number of vascular branches in the tissue construct may be determined to be similar to the number of vascular branches in biological tissues. If the average value of the number of vascular branches in the tissue construct is 2.5 or more and 4.5 or less or 3.0 or more and 4.2 or less, for example, the number of vascular branches in the tissue construct may be determined to be similar to the number of vascular branches in biological tissues. If the average value of the vascular interbranch lengths in the tissue construct to the average value of the vascular interbranch lengths in biological tissues is 80% or more and 150% or less, 85% or more and 130% or less, or 90% or more and 120% or less, for example, the vascular interbranch lengths in the tissue construct may be determined to be similar to the vascular interbranch lengths in biological tissues. In biological tissues, both thick blood vessels and thin blood vessels are observed. In view of this, if both blood vessels of large diameter (e.g., 10 μm or more and less than 25 μm) and blood vessels of small diameter (e.g., more than 0 μm and less than 10 μm) are observed like biological tissues, for example, determination may be made as having diversity of vascular diameter similar to that in biological tissues. If 60% or more, 70% or more, or 80% or more of all of the vascular diameters are distributed within more than 0 μm and less than 25 μm, for example, determination may be made as having diversity of vascular diameter similar to that in biological tissues. If the tissue construct includes adipocytes, it is preferable that the tissue construct include a vascular network among adipocytes. In this case, it is preferable, in addition to comprising a vascular network, that the adipocytes to be surrounded by the blood vessels be similar to those in biological tissues. If the average value of the size of the lipid droplet of the adipocytes in the tissue construct according to the present embodiment is 20 μm to 180 μm or 100 μm to 180 μm, for example, the tissue construct may be determined to include adipocytes similar to those in biological tissues. In the above comparison between biological tissues and the tissue construct, biological tissues and the tissue construct are compared under the same conditions (e.g., per certain specified volume, per certain specified area in the case of image analysis, per certain specified sample).

If the tissue construct is a three-dimensional tissue construct, it is preferable that the thickness of the three-dimensional tissue construct be 10 μm or more, it is more preferable that the thickness be 100 μm or more, and it is even more preferable that the thickness be 1000 μm or more. Such a three-dimensional tissue construct has a more similar structure to those of biological tissues, thus being preferable as an alternative for an experimental animal and a material for transplantation. The upper limit of the thickness of the three-dimensional tissue construct is not limited in any way, and may be, for example, 10 mm or less, or 3 mm or less, or 2 mm or less, or 1.5 mm or less, or 1 mm or less.

Here, if the three-dimensional tissue construct is sheet-like or cuboidal, the "thickness of the three-dimensional tissue construct" refers to the distance between the edges in the direction perpendicular to the principal plane. If unevenness is present in the principal plane, the thickness refers to the distance at the thinnest portion in the principal plane.

If the three-dimensional tissue construct is spherical or generally spherical, the thickness refers to the diameter. Or, if the three-dimensional tissue construct is ellipsoidal or generally ellipsoidal, the thickness refers to the minor axis. If the three-dimensional tissue construct is generally spherical or generally ellipsoidal and unevenness is present in the surface, the thickness refers to the shortest distance among distances between two points at which a line passing through the center of gravity of the three-dimensional tissue construct and the surface intersect.

The method of the present embodiment includes incubating cells comprising at least fat-derived stem cells in the presence of horse serum. Differentiation of fat-derived stem cells into vascular cells is promoted by incubating in the presence of horse serum.

Since it is only required that the differentiation is promoted through the process that at least some of the fat-derived stem cells come into contact with horse serum, any production method may be used without limitation in producing a tissue construct by the method of the present embodiment, and the production method may be three-dimensional culture or two-dimensional culture. In the method of the present embodiment, a tissue construct comprising vascular cells can be eventually produced by promoting the differentiation with fat-derived stem cells included in a tissue construct, or by promoting the differentiation in a situation that a tissue construct is formed in such a manner that fat-derived stem cells are included in the tissue construct. Accordingly, incubating cells comprising at least fat-derived stem cells in the presence of horse serum may be incubating only cells in the presence of horse serum, or incubating in the presence of horse serum in a state that cells and an extracellular matrix component are mixed together, or incubating in the presence of horse serum in a state that a tissue construct comprising cells and an extracellular matrix component is formed.

Production of a tissue construct by two-dimensional culture can be carried out with a known method to culture cells planarly. Examples thereof include a method including adding cells and a culture medium onto a substrate and culturing the cells, and a method including coating a substrate with gel, adding cells and a culture medium onto the coating, and culturing the cells. For the gel to coat a substrate, the above-mentioned fibrin gel, hydrogel, Matrigel, collagen gel, gelatin gel, and so on can be used.

Production of a tissue construct by three-dimensional culture can be carried out with a known method as well, and a preferred example to produce a three-dimensional tissue construct by using a fragmented extracellular matrix component will be described later.

Although horse serum (HS) can be produced by using a conventional method, commercially available horse serum may be used. Examples of commercially available horse serum include S0900 (BioWest), SH30074.02 (Cytiva), and 16050130 (Thermo Fisher Scientific).

Incubating in the presence of horse serum may be, for example, incubating (culturing) cells comprising at least fat-derived stem cells in a culture medium comprising horse serum.

The culture medium is not limited in any way, and a preferred culture medium can be selected according to the type of the cells to be cultured. The culture medium may be a solid culture medium or a liquid culture medium, but it is preferable that the culture medium be a liquid culture medium. Examples of the culture medium include the culture media Eagle's MEM, DMEM, F12K Medium, Modified Eagle Medium (MEM), Minimum Essential Medium, RPMI, and GlutaMax Medium. For the liquid culture medium, a gelatinous culture medium like fibrin gel, hydrogel, Matrigel, collagen gel, and gelatin gel may be used. Cells may be added to a gelatinous liquid culture medium, and a liquid culture medium comprising cells may be gelled. The culture medium may be a culture medium comprising serum other than horse serum, or a culture medium not comprising serum other than horse serum. The culture medium may be a mixed culture medium obtained by mixing two culture media.

The amount of horse serum may be 20 to 400 μL, 20 to 240 μL, or 160 to 240 μL per $1\times10^4$ fat-derived stem cells.

In the case of incubating the cells comprising at least fat-derived stem cells in a culture medium comprising horse serum, the content of horse serum in the culture medium may be, for example, 1% or more and 20% or less, 3% or more and 17% or less, 4% or more and 15% or less, or 5% or more and 12% or less, or 1% or more, 2% or more, 3% or more, 4% or more, 5% or more, 6% or more, 7% or more, 8% or more, 9% or more, or 10% or more, and 20% or less, 18% or less, 16% or less, 14% or less, or 12% or less.

The cell density in the culture medium before incubation can be appropriately determined according to the shape and thickness of the intended tissue, the size of the culture vessel, and so on. For example, the cell density in the culture medium may be 1 to $10^8$ cells/mL, or $10^3$ to $10^7$ cells/mL, or $10^5$ to $10^6$ cells/mL.

Incubation can be carried out under preferred conditions according to the type of the cells to be cultured, without any limitation. For example, the temperature in incubation may be 20° C. to 40° C., or 30° C. to 37° C. The pH of the culture medium may be 6 to 8, or 7.2 to 7.4. The time period of incubation may be 24 hours or more and 336 hours or less, or 72 hours or more and 336 hours or less, or 96 hours or more and 288 hours or less. The time period of the incubation in the presence of horse serum may be 24 hours or more and 336 hours or less, or 72 hours or more and 336 hours or less, or 96 hours or more and 288 hours or less. The time period of the incubation in the presence of horse serum may be 72 hours or more, 84 hours or more, 96 hours or more, 108 hours or more, 120 hours or more, 132 hours or more, or 144 hours or more, and 336 hours or less, 312 hours or less, 288 hours or less, 264 hours or less, 240 hours or less, or 226 hours or less.

The culture vessel (support) to be used for culture of the cells is not limited in any way, and may be, for example, a well insert, a low attachment plate, or a plate, for example, having a U-shaped or V-shaped bottom. The cells may be cultured with adhering to a support, the cells may be cultured without adhering to a support, and the cells may be cultured with the cells separated from a support at the middle of culturing. If the cells are cultured without adhering to a support or cultured with the cells separated from a support at the middle of culturing, it is preferable to use a plate, for example, having a U-shaped or V-shaped bottom or a low attachment plate, which inhibits the cells from adhering to a support.

The method of the present embodiment may include incubating cells comprising at least fat-derived stem cells together with a fragmented extracellular matrix component in the presence of horse serum. By incubating together with a fragmented extracellular matrix component, a three-dimensional tissue construct in which cells are three-dimensionally disposed via the fragmented extracellular matrix component can be obtained. It is preferable that the three-dimensional tissue construct be such that the fragmented extracellular matrix component is disposed in a gap among the cells. Cells in the cells may be the same type of cells, or different types of cells.

The fragmented extracellular matrix component can be obtained by fragmenting an extracellular matrix component. Herein, the "extracellular matrix component" is an aggregate of extracellular matrix molecules formed of a plurality of extracellular matrix molecules. The extracellular matrix refers to a substance present outside of cells in organisms. Any substance can be used for the extracellular matrix as long as the substance does not adversely affect the growth of cells and the formation of a cell aggregate. Specific examples thereof include, but are not limited to, collagen, elastin, proteoglycan, fibronectin, hyaluronic acid, laminin, vitronectin, tenascin, entactin, and fibrillin. One of these may be used singly and these may be used in combination as the extracellular matrix component. The extracellular matrix component may contain, for example, a collagen component, or be a collagen component. It is preferable for the extracellular matrix component in the present embodiment to be a substance present outside of animal cells, that is, an animal extracellular matrix component.

The extracellular matrix molecule may be a modified product or variant of the above-mentioned extracellular matrix molecule as long as the extracellular matrix molecule does not adversely affect the growth of cells and the formation of a cell aggregate, and may be a polypeptide such as a chemically synthesized peptide. The extracellular matrix molecule may be an extracellular matrix molecule having repeated sequences each represented by Gly-X-Y, which are characteristic to collagen. Here, Gly represents a glycine residue, and X and Y each independently represent an arbitrary amino acid residue. A plurality of Gly-X-Y may be the same or different. Because constraints on the disposition of molecular chains are reduced by inclusion of repeated sequences each represented by Gly-X-Y, much better functions, for example, as a scaffold material in cell culture are provided. The proportion of the sequence represented by Gly-X-Y in the extracellular matrix molecule having repeated sequences each represented by Gly-X-Y may be 80% or more and is preferably 95% or more based on the total amino acid sequence. The extracellular matrix molecule may be a polypeptide having an RGD sequence. The RGD sequence refers to a sequence represented by Arg-Gly-Asp (arginine residue-glycine residue-aspartic acid residue). Because cell adhesion is much more promoted by inclusion of an RGD sequence, much better functions, for example, as a scaffold material in cell culture are provided. Examples of extracellular matrix molecules containing a sequence represented by Gly-X-Y and an RGD sequence include collagen, fibronectin, vitronectin, laminin, and cadherin.

Examples of collagen include fibrous collagen and nonfibrous collagen. The fibrous collagen refers to collagen to serve as a main component of collagen fibers, and specific examples thereof include collagen I, collagen II, and collagen III. Examples of the nonfibrous collagen include collagen IV.

Examples of proteoglycan include, but are not limited to, chondroitin sulfate proteoglycan, heparan sulfate proteoglycan, keratan sulfate proteoglycan, and dermatan sulfate proteoglycan.

The extracellular matrix component may contain at least one selected from the group consisting of collagen, laminin, and fibronectin because the advantageous effect of the present invention becomes more significant, and it is preferable that the extracellular matrix component contain collagen. The collagen is preferably fibrous collagen, and more preferably collagen I. A commercially available collagen may be used as the fibrous collagen, and specific examples thereof include porcine skin-derived collagen I manufactured by NH Foods Ltd.

The extracellular matrix component may be an animal-derived extracellular matrix component. Examples of the animal species as the origin of the extracellular matrix component include, but are not limited to, humans, pigs, and bovines. For the extracellular matrix component, a component derived from one animal species may be used, and components derived from a plurality of animal species may be used in combination.

"Fragmenting" refers to reducing the size of an aggregate of the extracellular matrix molecule. Fragmentation may be carried out under conditions that cleave bonds in the extracellular matrix molecule, or under conditions that do not cleave any bond in the extracellular matrix molecule. The molecular structure of an extracellular matrix fragmented by application of physical force is typically unchanged from that before being fragmented (the molecular structure is maintained), in contrast to the case with enzymatic treatment. The fragmented extracellular matrix component may contain a defibered extracellular matrix component, which is a component obtained by defibering the above-mentioned extracellular matrix component by application of physical force. Defibering is a mode of fragmentation, and carried out, for example, under conditions that do not cleave any bond in the extracellular matrix molecule.

The method for fragmenting the extracellular matrix component is not limited in any way. The extracellular matrix component may be defibered by application of physical force such as an ultrasonic homogenizer, a stirring homogenizer, and a high-pressure homogenizer, as the method of defibering the extracellular matrix component. If a stirring homogenizer is used, the extracellular matrix component may be directly homogenized, or homogenized in an aqueous medium such as physiological saline. In addition, a millimeter-sized or nanometer-sized defibered extracellular matrix component can be obtained by adjusting the time, rotational frequency, and so on of homogenization. A defibered extracellular matrix component can be obtained also by defibering through repeated freezing and thawing.

The fragmented extracellular matrix component may at least partly contain a defibered extracellular matrix component. Alternatively, the fragmented extracellular matrix component may consist only of a defibered extracellular matrix component. In other words, the fragmented extracellular matrix component may be a defibered extracellular matrix component. It is preferable that the defibered extracellular matrix component contain a defibered collagen component. It is preferable that the defibered collagen component maintain the triple helix structure derived from collagen. The defibered collagen component may be a component that partially maintains the triple helix structure derived from collagen.

Examples of the shape of the fragmented extracellular matrix component include being fibrous. Being fibrous refers to a shape composed of a collagen component that is filamentous, or a shape composed of an extracellular matrix component that is filamentous and intermolecularly cross-linked. At least part of the fragmented extracellular matrix component may be fibrous. A filamentous product formed by aggregation of a plurality of filamentous extracellular matrix molecules (fibril), a filamentous product formed by additional aggregation of fibrils, and a product obtained by defibering any of them, and so on fall within the fibrous extracellular matrix component. In the fibrous extracellular matrix component, RGD sequences are conserved without being broken.

The average length of the fragmented extracellular matrix component may be 100 nm or more and 400 μm or less, or 100 nm or more and 200 μm or less. In an embodiment, the average length of the fragmented extracellular matrix component may be 5 μm or more and 400 μm or less, or 10 μm or more and 400 μm or less, or 22 μm or more and 400 μm or less, or 100 μm or more and 400 μm or less. In another embodiment, from the viewpoint of achieving much better redispersibility, the average length of the fragmented extracellular matrix component may be 100 μm or less, or 50 μm or less, or 30 μm or less, or 15 μm or less, or 10 μm or less, or 1 μm or less, and 100 nm or more. It is preferable that the average length of a large proportion of the fragmented extracellular matrix component to the entire fragmented extracellular matrix component be within the above numerical range. Specifically, it is preferable that the average length of 95% of the fragmented extracellular matrix component to the entire fragmented extracellular matrix component be within the above numerical range. It is preferable that the fragmented extracellular matrix component be a fragmented collagen component with the average diameter being within the above range, and it is more preferable that the fragmented extracellular matrix component be a defibered collagen component with the average diameter being within the above range.

The average diameter of the fragmented extracellular matrix component may be 10 nm or more and 30 μm or less, or 30 nm or more and 30 μm or less, or 50 nm or more and 30 μm or less, or 100 nm or more and 30 μm or less, or 1 μm or more and 30 μm or less, or 2 μm or more and 30 μm or less, or 3 μm or more and 30 μm or less, or 4 μm or more and 30 μm or less, or 5 μm or more and 30 μm or less. It is preferable that the fragmented extracellular matrix component be a fragmented collagen component with the average diameter being within the above range, and it is more preferable that the fragmented extracellular matrix component be a defibered collagen component with the average diameter being within the above range.

The average length and average diameter of the fragmented extracellular matrix component can be determined by individually measuring the fragmented extracellular matrix component with an optical microscope and performing image analysis. Herein, "average length" refers to the average value of length in the longitudinal direction of a sample measured, and "average diameter" refers to the average value of length in the direction orthogonal to the longitudinal direction of a sample measured.

The fragmented extracellular matrix component may contain, for example, a fragmented collagen component, and may consist of a fragmented collagen component. The "fragmented collagen component" refers to a product that is obtained by fragmenting a collagen component such as a fibrous collagen component and retains the triple helix structure. It is preferable that the average length of the fragmented collagen component be 100 nm to 200 μm, it is more preferable that the average length be 22 μm to 200 μm, and it is even more preferable that the average length be 100 μm to 200 μm. It is preferable that the average diameter of the fragmented collagen component be 50 nm to 30 μm, it is more preferable that the average diameter be 4 pun to 30 μm, and it is even more preferable that the average diameter be 20 μm to 30 μm.

At least part of the fragmented extracellular matrix component may be intermolecularly or intramolecularly crosslinked. The extracellular matrix component may be intermolecularly or intramolecularly crosslinked in the extracellular matrix molecules constituting the extracellular matrix component.

Examples of the crosslinking method include, though the method is not limited in any way, physical crosslinking by application of heat, ultraviolet rays, radiation, or the like and chemical crosslinking with a crosslinking agent or by enzymatic reaction or the like. Physical crosslinking is preferred from the viewpoint that the growth of cells is not inhibited. The crosslinking (any of physical crosslinking and chemical crosslinking) may be crosslinking via covalent bonds.

If the extracellular matrix component contains a collagen component, crosslinks may be formed between collagen molecules (triple helix structures), or between collagen fine fibers formed of collagen molecules. The crosslinking may be crosslinking by heat (thermal crosslinking). Thermal crosslinking can be carried out, for example, by performing heat treatment under reduced pressure with use of a vacuum pump. If thermal crosslinking of the collagen component is performed, the extracellular matrix component may be crosslinked through formation of a peptide bond (—NH—CO—) between an amino group of a collagen molecule and a carboxy group of the same or another collagen molecule.

Alternatively, the extracellular matrix component can be crosslinked by using a crosslinking agent. The crosslinking agent may be, for example, a crosslinking agent capable of crosslinking a carboxyl group and an amino group, or a crosslinking agent capable of crosslinking amino groups. For example, aldehyde-based, carbodiimide-based, epoxide-based, and imidazole-based crosslinking agents are preferred as the crosslinking agent from the viewpoint of economic efficiency, safety, and operability, and specific examples thereof include glutaraldehyde and water-soluble carbodiimides such as 1-ethyl-3-(3-dimethylaminopropyl) carbodiimide hydrochloride and 1-cyclohexyl-3-(2-morpholinyl-4-ethyl) carbodiimide sulfonate.

Quantification of the degree of crosslinking can be appropriately selected according to the type of the extracellular matrix component, the means for crosslinking, and so on. The degree of crosslinking may be 1% or more, 2% or more, 4% or more, 8% or more, or 12% or more, and may be 30% or less, 20% or less, or 15% or less. With the degree of crosslinking being in the above range, the extracellular matrix molecules can be moderately dispersed, and redispersibility after dry storage is satisfactory.

If amino groups in the extracellular matrix component are used for crosslinking, the degree of crosslinking can be quantified on the basis of a TNBS (trinitrobenzenesulfonic acid) method. The degree of crosslinking determined by the TNBS method may be in the above-mentioned range. The degree of crosslinking determined by the TNBS method is the proportion of amino groups used for crosslinking among the amino groups possessed by the extracellular matrix. If the extracellular matrix component contains a collagen component, it is preferable that the degree of crosslinking as measured by the TNBS method be within the above range.

The degree of crosslinking may be calculated by quantifying carboxyl groups. In the case of a water-insoluble extracellular matrix component, for example, quantification may be made by using a TBO (toluidine blue O) method. The degree of crosslinking determined by the TBO method may be within the above-mentioned range.

The content of the extracellular matrix component in the tissue construct (e.g., a three-dimensional tissue construct)

may be 0.01 to 90% by mass based on the tissue construct (dry weight), it is preferable that the content be 10 to 90% by mass, it is preferable that the content be 10 to 80% by mass, it is preferable that the content be 10 to 70% by mass, it is preferable that the content be 10 to 60% by mass, it is preferable that the content be 1 to 50% by mass, it is preferable that the content be 10 to 50% by mass, it is more preferable that the content be 10 to 30% by mass, and it is more preferable that the content be 20 to 30% by mass.

Here, the "extracellular matrix component in the tissue construct" refers to the extracellular matrix component constituting the tissue construct, and may be derived from an endogenous extracellular matrix component or derived from an exogenous extracellular matrix component.

The "endogenous extracellular matrix component" refers to an extracellular matrix component produced by extracellular matrix-producing cells. Examples of extracellular matrix-producing cells include the above-mentioned mesenchymal cells such as fibroblasts, chondrocytes, and osteoblasts. The endogenous extracellular matrix component may be fibrous or nonfibrous.

The "exogenous extracellular matrix component" refers to an extracellular matrix component supplied from the external. The animal species as the origin of the exogenous extracellular matrix component may be identical to or different from the animal species as the origin of the endogenous extracellular matrix component. Examples of the animal species as the origin include humans, pigs, and bovines. The exogenous extracellular matrix component may be an artificial extracellular matrix component.

If the extracellular matrix component is a collagen component, the exogenous extracellular matrix component is also referred to as an "exogenous collagen component", and the "exogenous collagen component", referring to a collagen component supplied from the external, is an aggregate of collagen molecules formed of a plurality of collagen molecules, and specific examples thereof include fibrous collagen and nonfibrous collagen. It is preferable that the exogenous collagen component be fibrous collagen. The fibrous collagen refers to a collagen component to serve as a main component of collagen fibers, and examples thereof include collagen I, collagen II, and collagen III. A commercially available collagen may be used as the fibrous collagen, and specific examples thereof include porcine skin-derived collagen I manufactured by NH Foods Ltd. Examples of exogenous nonfibrous collagen include collagen IV.

The animal species as the origin of the exogenous extracellular matrix component may be different from the animal species as the origin of the cells. If the cells include extracellular matrix-producing cells, the animal species as the origin of the exogenous extracellular matrix component may be different from the animal species as the origin of the extracellular matrix-producing cells. In other words, the exogenous extracellular matrix component may be a xenogeneic extracellular matrix component.

Specifically, if the tissue construct contains an endogenous extracellular matrix component and a fragmented extracellular matrix component, the content of the extracellular matrix component constituting the tissue construct refers to the total amount of the endogenous extracellular matrix component and the fragmented extracellular matrix component. The content of the extracellular matrix can be calculated from the volume of the tissue construct obtained and the mass of the tissue construct after being decellularized.

If the extracellular matrix component contained in the three-dimensional tissue construct is a collagen component, for example, examples of the method for quantifying the amount of the collagen component in the three-dimensional tissue construct include a method of quantifying hydroxyproline as follows. Hydrochloric acid (HCl) is mixed into a lysate obtained by lysing the three-dimensional tissue construct, incubation is performed at high temperature for a predetermined period of time and the temperature is then returned to room temperature, and the supernatant resulting from centrifugation is diluted to a predetermined concentration to prepare a sample. Hydroxyproline standard solution is treated in the same manner as for the sample, and then serially diluted to prepare standards. Each of the sample and standards is subjected to a predetermined treatment with hydroxyproline assay buffer and a detection reagent, and the absorbance at 570 nm is measured. The amount of the collagen component is calculated by comparing the absorbance of the sample and those of the standards. Alternatively, a lysate obtained by suspending the three-dimensional tissue construct directly in hydrochloric acid of high concentration and lysing the three-dimensional tissue construct is centrifuged to collect the supernatant, which may be used for quantification of the collagen component. The three-dimensional tissue construct to be lysed may be as it is after recovery from the culture solution, or subjected to drying treatment after recovery and lysed with the liquid components removed. If the three-dimensional tissue construct as it is after recovery from the culture solution is lysed for quantification of the collagen component, however, the measurement of weight of the three-dimensional tissue construct is expected to vary because of the influence of a culture medium component absorbed by the three-dimensional tissue construct and a culture medium residue caused by improper experimental techniques, and hence it is preferable from the viewpoint of stable measurement of the amount of the collagen component to the weight of or per unit weight of the construct to base on the weight after drying.

More specific examples of the method for quantifying the amount of the collagen component include the following method.

(Preparation of Sample)

The whole of the three-dimensional tissue construct subjected to freeze-drying treatment is mixed with 6 mol/L HCl and incubated with a heat block at 95° C. for 20 hours or more, and the temperature is then returned to room temperature. Centrifugation is performed at 13000 g for 10 minutes, and the supernatant of the sample solution is then collected. Dilution is appropriately performed with 6 mol/L HCl so that results in measurement described later fall within the range of a calibration curve, and 200 μL of the resultant is then diluted with 100 μL of ultrapure water to prepare a sample. Of the sample, 35 μL is used.

(Preparation of Standards)

To a screw cap tube, 125 μL of standard solution (1200 μg/mL in acetic acid) and 125 μL of 12 mol/l HCl are added and mixed together, and incubated with a heat block at 95° C. for 20 hours, and the temperature is then returned to room temperature. Centrifugation is performed at 13000 g for 10 minutes, the supernatant is then diluted with ultrapure water to prepare 300 μg/mL S1, and S1 is serially diluted to produce S2 (200 μg/mL), S3 (100 μg/mL), S4 (50 μg/mL), S5 (25 μg/mL), S6 (12.5 μg/mL), and S7 (6.25 μg/mL). Additionally, S8 (0 μg/mL), which consists only of 90 μL of 4 mol/l HCl, is prepared.

(Assay)

The standards and the sample each in 35 μL are added to a plate (attached to a QuickZyme Total Collagen Assay kit, QuickZyme Biosciences). To each well, 75 μL of assay buffer (attached to the kit) is added. The plate is closed with a seal, and incubation is performed with shaking at room temperature for 20 minutes. The seal is removed, and 75 μL of detection reagent (reagent A:B=30 μL:45 μL, attached to the kit) is added to each well. The plate is closed with a seal, the solutions are mixed by shaking and incubated at 60° C. for 60 minutes. After sufficient cooling on ice, the seal is removed, and absorbance at 570 nm is measured. The amount of the collagen component is calculated by comparing the absorbance of the sample and those of the standards.

The collagen component occupying in the tissue construct may be specified by the area ratio or volume ratio. "Specifying by the area ratio or volume ratio" refers to calculating the ratio of the existence area of the collagen component to the entire of the tissue construct by any of visual observation, various microscopes, image analysis software, and so on after the collagen component in the tissue construct is made distinguishable from other tissue construct constituents, for example, with a known staining method (e.g., immunostaining using an anti-collagen antibody, or Masson's trichrome staining). In specifying by the area ratio, which cross-section or surface in the tissue construct is used to specify the area ratio is not limited, and if the tissue construct is a three-dimensional tissue construct and spherical or in like shape, for example, specification may be made by a diagram of a cross-section passing through the generally central portion.

If the collagen component in the tissue construct is specified by the area ratio, for example, the proportion of the area is 0.01 to 99% based on the total area of the tissue construct, it is preferable that the proportion of the area be 1 to 99%, it is preferable that the proportion of the area be 5 to 90%, it is preferable that the proportion of the area be 7 to 90%, it is preferable that the proportion of the area be 20 to 90%, and it is more preferable that the proportion of the area be 50 to 90%. The proportion of the area of the collagen component constituting the tissue construct refers to the proportion of the area of the total of the endogenous collagen component and exogenous collagen component. If the tissue construct obtained is stained with Masson's trichrome, for example, the proportion of the area of the collagen component can be calculated as the proportion of the area of the collagen component stained blue to the total area of a cross-section passing through the generally central portion of the tissue construct.

It is preferable that the remaining rate of the tissue construct after trypsin treatment with a trypsin concentration of 0.25% at a temperature of 37° C. and pH 7.4 for a reaction time of 15 minutes be 70% or more, it is more preferable that the remaining rate be 80% or more, and it is even more preferable that the remaining rate be 90% or more. Such a tissue construct is less likely to undergo decomposition by the enzyme during or after culture, thus being stable. The remaining rate can be calculated, for example, from the mass of the tissue construct before and after the trypsin treatment.

The remaining rate of the tissue construct after collagenase treatment with a collagenase concentration of 0.25% at a temperature of 37° C. and pH 7.4 for a reaction time of 15 minutes may be 70% or more, it is more preferable that the remaining rate be 80% or more, and it is even more preferable that the remaining rate be 90% or more. Such a tissue construct is less likely to undergo decomposition by the enzyme during or after culture, thus being stable.

Incubating cells comprising at least fat-derived stem cells together with a fragmented extracellular matrix component in the presence of horse serum may be, for example, incubating (culturing) the cells in a culture medium comprising horse serum and a fragmented extracellular matrix component. At that time, a culture medium comprising a fragmented extracellular matrix component and horse serum may be used in advance, horse serum may be added to a culture medium comprising a fragmented extracellular matrix component, and a fragmented extracellular matrix component may be added to a culture medium comprising horse serum.

A step of bringing the cells and the fragmented extracellular matrix component into contact in an aqueous medium may be further included before incubation. In this case, horse serum may be included in the aqueous medium, or added before incubation, or added during incubation. The aqueous medium may be the same as or different from that in incubation. By incubating with the cells and the fragmented extracellular matrix component being in contact in an aqueous medium, a three-dimensional tissue construct in which the fragmented extracellular matrix component is disposed in a gap among the cells and the cells and the fragmented extracellular matrix component are three-dimensionally distributed in a homogeneous manner can be produced. Therefore, if a step of bringing the cells and the fragmented extracellular matrix component into contact in an aqueous medium is further included, incubating cells comprising at least fat-derived stem cells in the presence of horse serum may be a step of incubating the cells brought into contact with the fragmented extracellular matrix component in the presence of horse serum. At that time, the tissue construct comprising vascular cells to be produced is a three-dimensional tissue construct comprising vascular cells.

The "aqueous medium" refers to a liquid containing water as an essential component. The aqueous medium is not limited in any way as long as the fragmented extracellular matrix component can be stably present. Examples of the aqueous medium include, but are not limited to, physiological saline such as phosphate-buffered saline (PBS) and liquid culture media such as Dulbecco's Modified Eagle Medium (DMEM), F12K Medium, and a culture medium specialized for vascular endothelial cells (EGM2).

It is preferable that the pH of the aqueous medium be in the range that does not adversely affect the growth of cells and the formation of a cell aggregate. From the viewpoint of reducing loads to the cells when the aqueous medium is put into the cells, the pH of the aqueous medium may be, for example, 7.0 or more, and 8.0 or less. Specifically, the pH of the aqueous medium may be 7.0, 7.1, 7.2, 7.3, 7.4, 7.5, 7.6, 7.7, 7.8, 7.9, or 8.0. It is preferable that the aqueous medium have buffering capacity in the above pH range, and more preferably the aqueous medium is a liquid culture medium. The liquid culture medium is not limited in any way, and a preferred culture medium can be selected according to the type of the cells to be cultured. Examples of the culture medium include the culture media Eagle's MEM, DMEM, F12K Medium, Modified Eagle Medium (MEM), Minimum Essential Medium, RPMI, and GlutaMax Medium. The culture medium may be a culture medium supplemented with serum or serum-free culture medium. Moreover, the liquid culture medium may be a mixed culture medium obtained by mixing two or more culture media.

When being dispersed in the aqueous medium, the fragmented extracellular matrix component readily comes into contact with the cells in the aqueous medium, and can promote the formation of a three-dimensional tissue construct. Examples of the contacting step include, but are not limited to, a method of mixing together an aqueous medium containing the fragmented extracellular matrix component and an aqueous medium containing the cells, a method of adding the cells to an aqueous medium containing the fragmented extracellular matrix component, a method of adding an aqueous medium containing the extracellular matrix component to a culture solution containing the cells, a method of adding the cells to an aqueous medium containing the extracellular matrix extracellular matrix component, and a method of adding the extracellular matrix component and the cells to an aqueous medium prepared in advance.

The concentration of the fragmented extracellular matrix component in the contacting step can be appropriately determined according to the shape and thickness of the intended three-dimensional tissue construct, the size of a culture vessel, and so on. For example, the concentration of the fragmented extracellular matrix component in the aqueous medium in the contacting step may be 0.1 to 90% by mass, or 1 to 30% by mass.

The amount of the fragmented extracellular matrix component in the contacting step may be, per $1.0\times10^6$ cells, for example, 0.1 to 100 mg, 0.5 to 50 mg, 0.8 to 25 mg, 1.0 to 10 mg, 1.0 to 5.0 mg, 1.0 to 2.0 mg, or 1.0 to 1.8 mg, and may be 0.7 mg or more, 1.1 mg or more, 1.2 mg or more, 1.3 mg or more, or 1.4 mg or more, and may be 7.0 mg or less, 3.0 mg or less, 2.3 mg or less, 1.8 mg or less, 1.7 mg or less, 1.6 mg or less, or 1.5 mg or less.

It is preferable that the mass ratio between the fragmented extracellular matrix component and the cells (fragmented extracellular matrix component/cells) in the contacting step be 1/1 to 1000/1, it is more preferable that the mass ratio be 9/1 to 900/1, and it is even more preferable that the mass ratio be 10/1 to 500/1.

The amount of the fragmented extracellular matrix component in the contacting step may be 0.1% by weight to 10% by weight, 0.5% by weight to 8% by weight, or 1 to 5% by weight based on the total weight of the culture medium.

An embodiment of the method for producing a three-dimensional tissue construct may include adding fibrinogen and thrombin simultaneously or separately in the contacting step, or after the contacting step before the culturing step. When fibrinogen and thrombin are mixed together, they react and fibrin is formed. The content of fibrinogen may be, for example, 1 to 10 mg/mL, or 2 to 8 mg/mL, or 5 to 6 mg/mL based on the culture medium.

A step of precipitating both the fragmented extracellular matrix component and the cells in the aqueous medium may be further included after the contacting step before incubation. The distribution of the extracellular matrix component and the cells in the three-dimensional tissue construct becomes more homogeneous by carrying out such a step. The specific method is not limited in any way, and examples thereof include a method of performing a centrifugal operation for a culture solution containing the fragmented extracellular matrix component and the cells.

The cell density in the culture medium before the above-described incubation may be the same as the cell density in the aqueous medium in the contacting step.

The present invention provides, as an embodiment, a method for promoting the differentiation of fat-derived stem cells, comprising incubating cells comprising at least fat-derived stem cells in the presence of horse serum. As described above, the differentiation of fat-derived stem cells into vascular cells can be promoted by incubating fat-derived stem cells in the presence of horse serum. The method of the present embodiment can be used even in tissue construct production including incubation of cells, and the tissue construct production may be by three-dimensional culture or by two-dimensional culture.

For specific modes and the like of the method of the present embodiment, including the cells, incubation, the fragmented extracellular matrix component, and the steps, the above-described specific modes and the like can be applied without limitation. For example, even in the method of the present embodiment, a step of bringing the cells and the fragmented extracellular matrix component into contact in the aqueous medium may be included before incubation.

Moreover, the method of the present embodiment may be a method for promoting the differentiation of fat-derived stem cells in a method for producing a three-dimensional tissue construct.

For specific modes and the like of the method of the present embodiment, including the three-dimensional tissue construct, the cells, incubation, the fragmented extracellular matrix component, and the steps, the above-described specific modes and the like can be applied without limitation.

EXAMPLES

Hereinafter, the present invention will be more specifically described on the basis of Examples. However, the present invention is not limited to Examples in the following.

Cells, reagents, a production method, and so on used for production of a tissue construct are as follows.

(Cells and Collagen)

Subcutaneous fat-derived stem cells (ADSCs, bovine-derived, collected from edible beef by a conventional method)

Fibrinogen from bovine plasma Type I-S(Sigma-Aldrich Co. LLC #F8630)

Horse serum (HS, Thermo Fisher Scientific #16050130)

Fetal bovine serum (FBS, Thermo Fisher Scientific #26140)

Calf serum (Calf serum, GE Health care #SH30118)

Human serum (Human serum, Lonza #4W-820)

(Culture Media and Solutions)

DMEM culture medium (high-glucose, NACALAI TESQUE, INC.)

F12K Medium (Thermo Fisher Scientific #21127022)

50 mg/mL fibrinogen stock solution: 50 mg of fibrinogen was weighed in an Eppendorf tube, and 1 mL of DMEM (0% FBS, 1% antibiotic) was immediately added thereto. After the tube was shaken by hand for mixing, the tube was placed in a water bath at 37° C. for 3 to 5 minutes, and the resultant was filtered through a filter of 0.2 μm in pore size and aliquoted into equal amounts in Eppendorf tubes for use.

Production Example 1

Tissue constructs were produced through two-dimensional culture as follows.

A 48-well plate (manufactured by IWAKI) was prepared. Into the wells, 5000 (cells/well) bovine subcutaneous fat-derived stem cells were seeded, and cultured with use of 1 mL of DMEM culture medium containing 10% fetal bovine serum, F12K Medium containing 10% fetal bovine serum, DMEM culture medium containing 10% horse serum, or F12K Medium containing 10% horse serum for 7 days.

FIG. 1 shows photographs of fluorescence observation with use of the confocal quantitative image cytometer CQ (Yokogawa Electric Corporation) for the obtained tissue constructs subjected to CD31 immunostaining. For each culture medium, "×4" and "×20" indicate being a photograph of observation at a magnification of 4 times (left) and 20 times (right), respectively.

No endothelium formation was found in the tissue constructs produced with the culture media containing fetal bovine serum. On the other hand, endothelium formation had progressed in the tissue construct produced with the F12K Medium containing horse serum, indicating that a vascular network was constructed. Difference due to the difference in medium type, DMEM culture medium and F12K Medium, was not found. It was demonstrated that the differentiation of fat-derived stem cells into vascular cells is promoted by addition of horse serum.

Production Example 2

Tissue constructs were produced through two-dimensional culture as follows.

A 48-well plate was prepared in the same manner as in Production Example 1. In 200 μL of F12K Medium or DMEM culture medium containing 10% horse serum, $5\times10^5$ cells/mL or $1\times10^6$ cells/mL of bovine subcutaneous fat-derived stem cells were cultured for 7 days and then seeded on the wells, and the tissue constructs obtained after 48 hours were evaluated by means of CD31 immunostaining and counterstaining with Hoechst.

Figure 2:
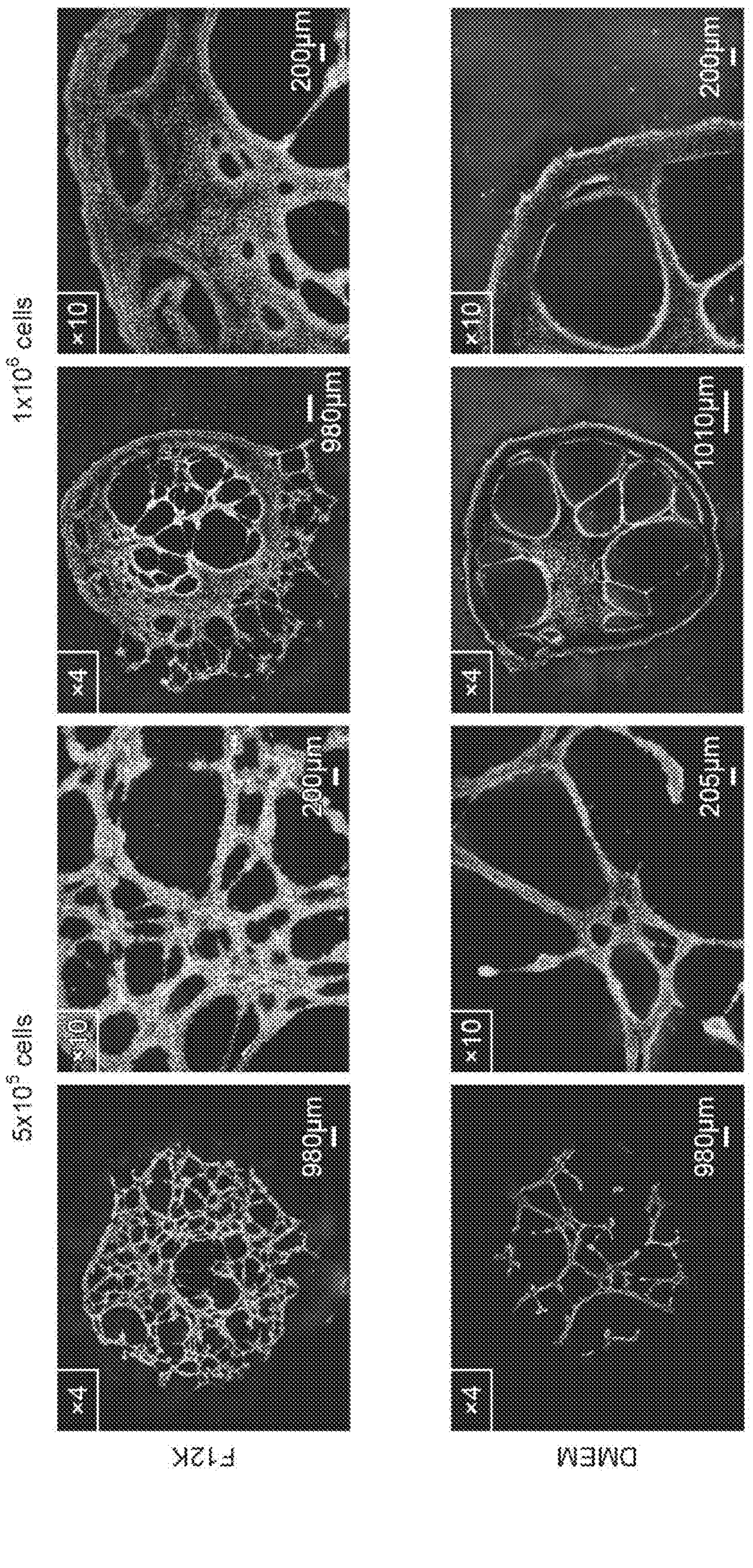
FIG. 2 shows results of CD31 immunostaining and counterstaining with Hoechst for tissue constructs produced in Production Example 2.

FIG. 2 shows photographs of fluorescence observation with use of the confocal quantitative image cytometer CQ (Yokogawa Electric Corporation). White dots observed in the right are nuclei.

For both the cell counts of $5\times10^5$ cells and $1\times10^6$ cells, it was found that an intercellular vascular network was constructed through endothelium formation. Difference due to the difference in medium type, DMEM culture medium and F12K Medium, was not found. It was demonstrated that the differentiation of fat-derived stem cells into vascular cells is promoted by addition of horse serum, irrespective of cell count.

Production Example 3

Tissue constructs were produced through two-dimensional culture as follows.

Into a 24-well or 48-well plate (manufactured by IWAKI), 5000 (cells/well) bovine subcutaneous fat-derived stem cells were seeded, and cultured in 1 mL of DMEM culture medium containing 1%, 5%, or 10% hours serum for 7 days, and tissue constructs were obtained.

Figure 3:
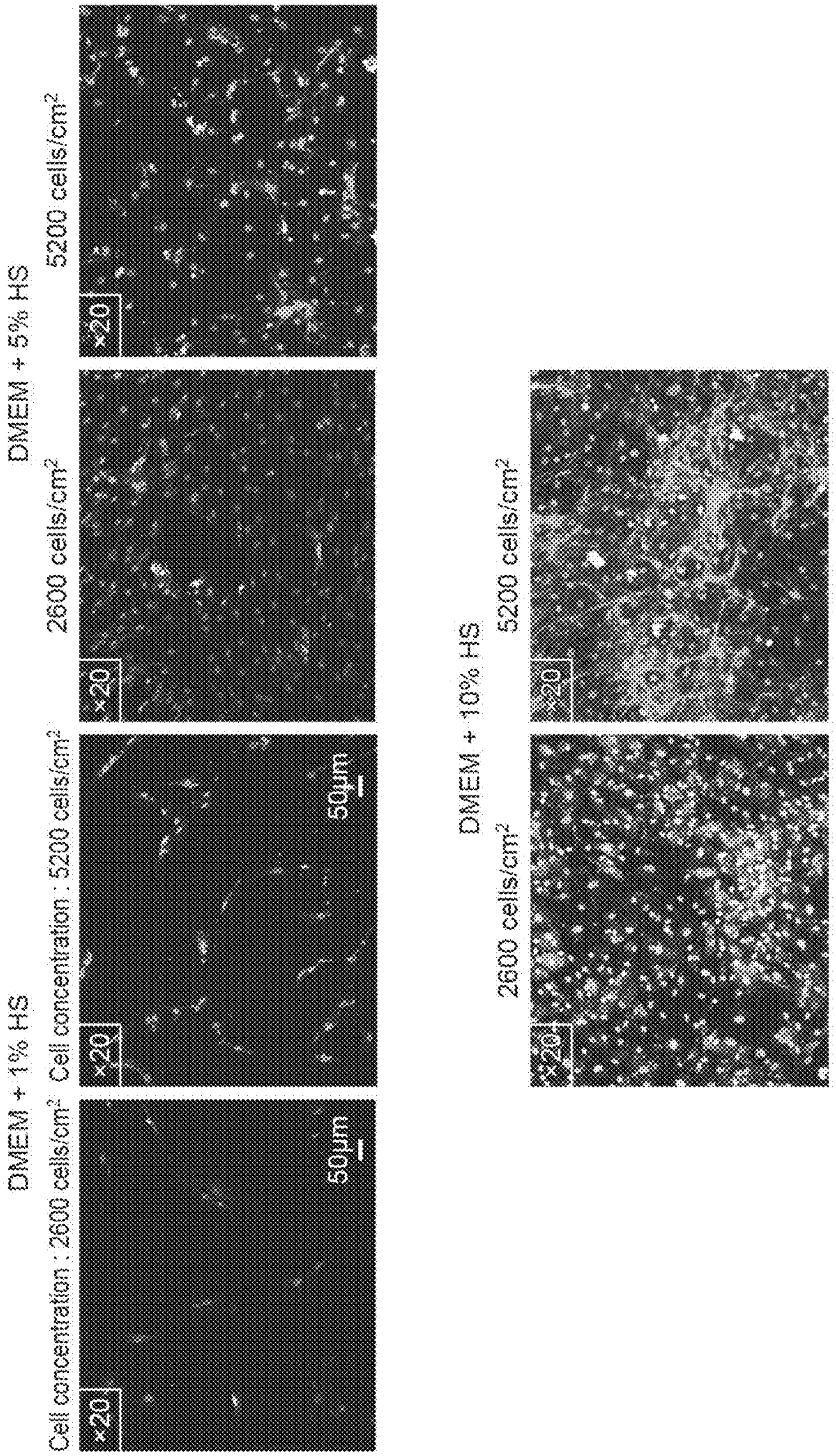
FIG. 3 shows results of CD31 immunostaining and counterstaining with Hoechst for tissue constructs produced in Production Example 3. White dots indicate nuclei (Hoechst staining).

The tissue constructs obtained were evaluated by means of CD31 immunostaining and counterstaining with Hoechst. FIG. 3 shows photographs of fluorescence observation with use of the confocal quantitative image cytometer CQ (Yokogawa Electric Corporation). For each horse serum content, a photograph with a cell concentration of 2600 (cells/cm$^2$) shows a result with use of the 24-well plate, and a photograph with a cell concentration of 5200 (cells/cm$^2$) shows a result with use of the 48-well plate.

It was found that as compared with the case with 1% horse serum, endothelium formation had proceeded in the case with 5% horse serum and endothelium formation had more proceeded in the case with 10% horse serum. It was demonstrated that the more horse serum is added, the more the differentiation of fat-derived stem cells into vascular cells is promoted.

Production Example 4

Tissue constructs were produced through two-dimensional culture as follows.

Into a 24-well or 48-well plate (manufactured by IWAKI), 5000 (cells/well) bovine subcutaneous fat-derived stem cells were seeded, and cultured in 1 mL of DMEM culture medium containing 10% fetal bovine serum, fetal bovine serum, horse serum, or human serum for 7 days, and tissue constructs were obtained.

Figure 4:
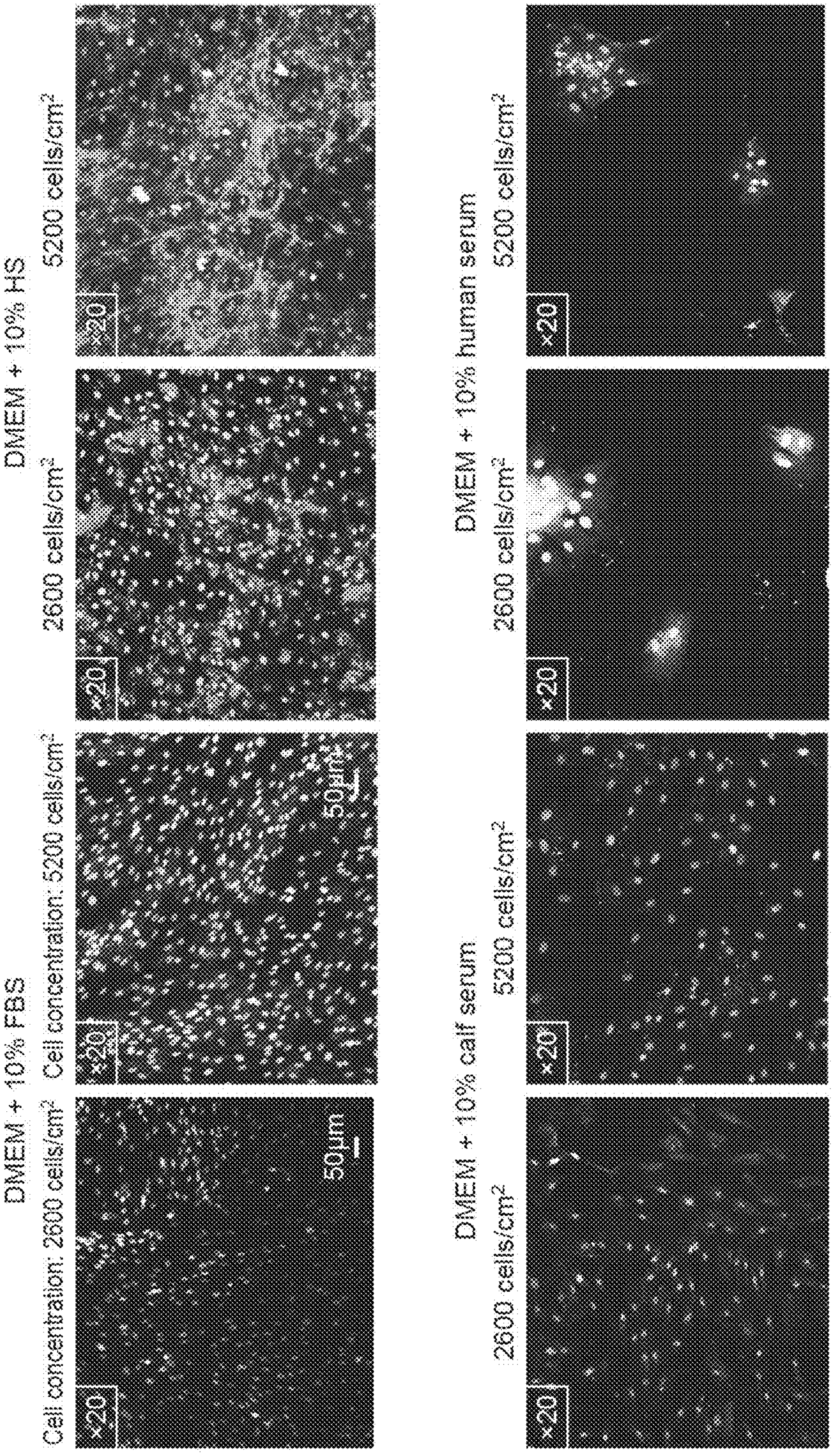
FIG. 4 shows results of CD31 immunostaining and counterstaining with Hoechst for tissue constructs produced in Production Example 4. White dots indicate nuclei (Hoechst staining).

The tissue constructs obtained were evaluated by means of CD31 immunostaining and counterstaining with Hoechst. FIG. 4 shows photographs of fluorescence observation with use of the confocal quantitative image cytometer CQ (Yokogawa Electric Corporation). For each culture medium, a photograph with a cell concentration of 2600 (cells/cm$^2$) shows a result with use of the 24-well plate, and a photograph with a cell concentration of 5200 (cells/cm$^2$) shows a result with use of the 48-well plate.

While it was found that an intercellular vascular network was constructed through endothelium formation in the tissue construct produced with use of horse serum, progression of endothelium formation to such a degree was not found in the tissue constructs produced by using fetal bovine serum, fetal bovine serum, or human serum. Clearly, endothelium formation had more proceeded in the case with horse serum than the cases with other serum. From this, it was demonstrated that the differentiation of fat-derived stem cells into vascular cells is promoted by addition of horse serum.

Production Example 5

Three-dimensional tissue constructs were produced through three-dimensional culture as follows.

By heating 100 mg of a sponge fragment of porcine skin-derived collagen I (manufactured by NH Foods Ltd.) at 200° C. for 24 hours, a collagen component at least part of which was crosslinked (crosslinked collagen component) was obtained. No large change in appearance was found in collagen after the heating at 200° C. Into a 15-mL tube, 50 mg of the crosslinked collagen component was put, to which 5 mL of ultrapure water was added, and homogenization was performed by using a homogenizer (AS ONE Corporation VH-10) for 6 minutes to defiber the crosslinked collagen component.

Centrifugation was performed at 10000 rpm under 21° C. for 10 minutes. The supernatant was sucked, and the collagen pellet was mixed with 5 mL of fresh ultrapure water to produce a collagen solution. An operation in which the tube containing the collagen solution with being kept on ice was ultrasonicated with a sonicator (Sonics and Materials, Inc. VC50) at 100 V for 20 seconds, the sonicator was removed, and the tube containing the collagen solution was cooled on ice for 10 seconds was repeated 100 times, and thereafter the collagen solution was filtered through a filter of 40 μm in pore size to afford a dispersion containing a defibered collagen component (CMF). The dispersion was freeze-dried by using a conventional method to afford a defibered collagen component (CMF) as a dried product. The average length (length) of CMF was 14.8±8.2 μm (N=20).

After fragmented collagen was dispersed in a culture medium (F12K) to reach a concentration of 10 mg/mL, fibrinogen and cells were mixed to give a mixture of a defibered collagen component (final concentration: 1.2% by weight), fibrinogen (final concentration: 6 mg/mL), and bovine subcutaneous fat-derived stem cells (final concentration: $2\times10^6$ cells/mL), and 30 μL of the mixture was seeded into the 24-well plate Transwell (manufactured by IWAKI). The mixture seeded was cultured with addition of 2 mL of a culture medium containing 10% horse serum. Culture was performed until day 10 of culture, with the culture medium replaced every 2 days, and three-dimensional tissue constructs were obtained.

Figure 5:
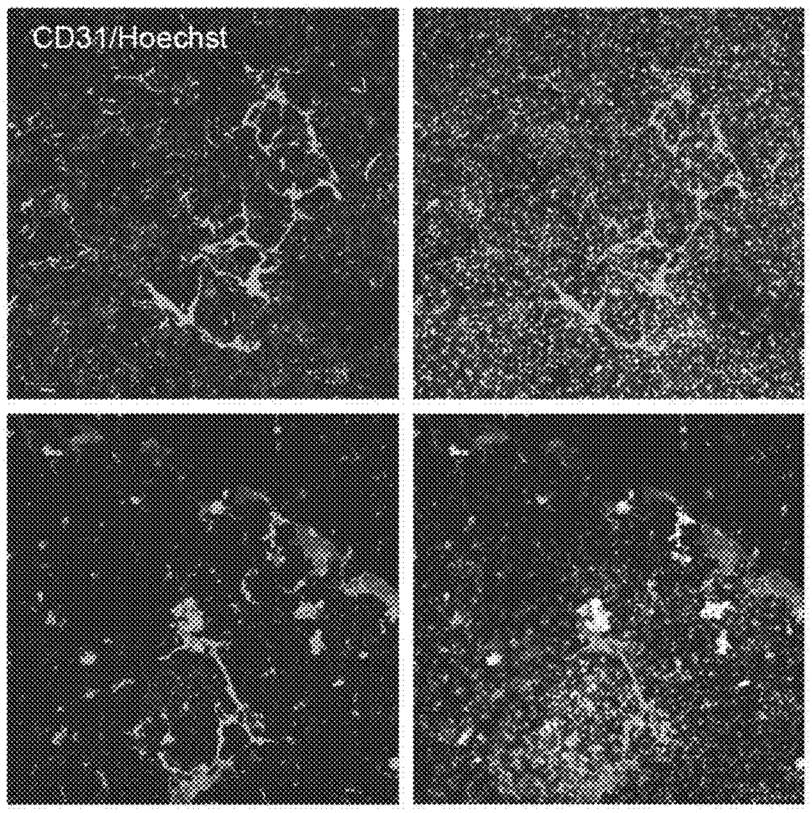
FIG. 5 shows results of CD31 immunostaining and counterstaining with Hoechst for tissue constructs produced in Production Example 5. White dots indicate nuclei (Hoechst staining).

The three-dimensional tissue constructs obtained were subjected to CD31 immunostaining, and nuclei were stained by Hoechst staining. FIG. 5 shows photographs of fluorescence observation with use of the confocal quantitative image cytometer CQ (Yokogawa Electric Corporation). The left photographs are photographs of observation only for CD31 immunostaining, and the right photographs are photographs of observation for CD31 immunostaining and Hoechst staining. White dots observed in the right are nuclei.

It was found that an intercellular vascular network was constructed through endothelium formation in the three-dimensional tissue construct produced with the F12K Medium containing 10% horse serum. It was demonstrated that the differentiation of fat-derived stem cells into vascular cells is promoted by addition of horse serum.

Production Example 6

Tissue constructs were produced through two-dimensional culture as follows, and culture of bovine subcutaneous fat-derived stem cells and the differentiation into bovine endothelial cells were observed.

A 48-well plate (manufactured by IWAKI) was prepared. Into the wells, 5000 (cells/well) bovine subcutaneous fat-derived stem cells of first passage cultured in advance in DMEM culture medium were seeded, and cultured with use of any of the following eight different culture media for 7 days, with the culture medium replaced every 2 to 3 days.

(1) DMEM culture medium containing 1% horse serum
(2) DMEM culture medium containing 5% horse serum
(3) DMEM culture medium containing 10% horse serum
(4) DMEM culture medium containing 10% fetal bovine serum
(5) DMEM culture medium containing 10% human serum
(6) DMEM culture medium containing 10% calf serum
(7) F12K Medium containing 10% horse serum
(8) F12K Medium containing 10% fetal bovine serum The culture media of (1) to (8) each contains 1% antibacterial drug-antifungal drug mixed solution.

Figure 6:
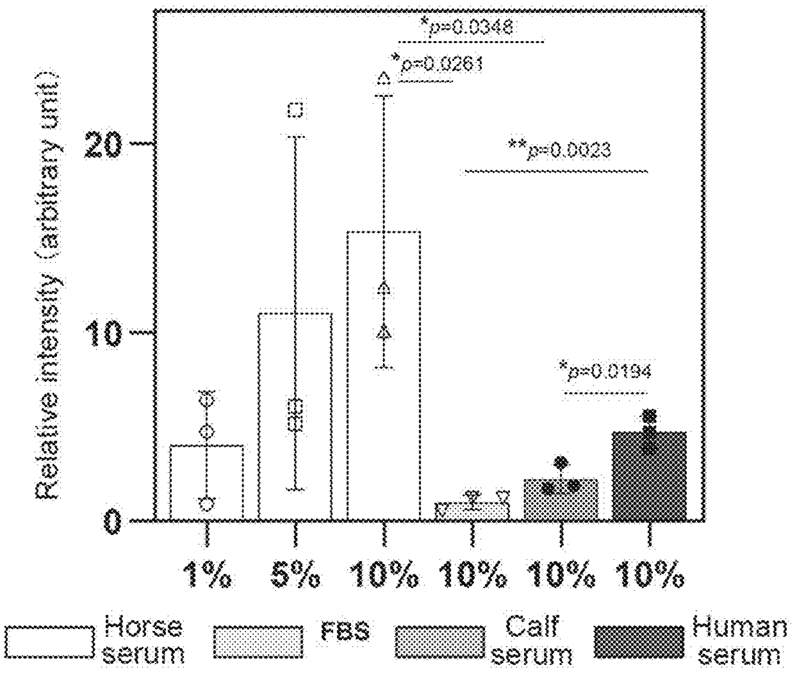
FIG. 6 shows results of quantification by CD31 immunostaining for tissue constructs produced in Production Example 6.

FIG. 6 shows results of comparison by difference in serum conditions in DMEM culture medium for the obtained tissue constructs subjected to quantification (n=3) by CD31 immunostaining quantification (one-way unpaired ANOVA with a Tukey's HSD post-test). It was demonstrated that the differentiation of fat-derived stem cells into endothelial cells was promoted in the case with addition of horse serum, in particular, in the cases with addition of 5% or 10% horse serum.

Figure 7:
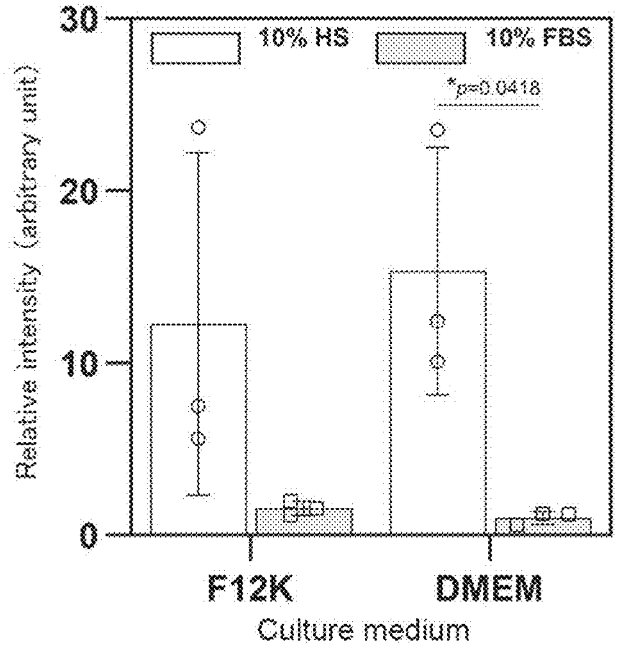
FIG. 7 shows results of quantification by CD31 immunostaining for tissue constructs produced in Production Example 6.

FIG. 7 shows results with 10% horse serum and those with 10% fetal bovine serum in different base culture media for the obtained tissue constructs subjected to quantification (n=3) by CD31 immunostaining (two-ways unpaired ANOVA with a Sidak post-test). It was demonstrated that the differentiation of fat-derived stem cells into endothelial cells was more promoted in the tissue constructs produced with the F12K Medium or DMEM culture medium containing 10% horse serum than in the tissue constructs produced with the F12K Medium or DMEM culture medium containing 10% fetal bovine serum. Also in this case, significant difference due to the difference in medium type, DMEM culture medium and F12K Medium, was not found.

The invention claimed is:

1. A method for producing a tissue construct comprising vascular cells, comprising incubating cells comprising at least bovine fat-derived stem cells in a culture medium comprising horse serum in an amount of 5 to 20% of the culture medium,
wherein the incubating is performed for 144 hours or more.

2. The method according to claim 1, wherein the tissue construct comprising vascular cells comprises a vascular network.

3. The method according to claim 1, wherein the cells comprising at least bovine fat-derived stem cells comprise no vascular cell.

4. The method according to claim 1, wherein the incubating in the presence of horse serum is incubating in a culture medium comprising the horse serum.

5. The method according to claim 1, wherein the culture medium further comprises a fragmented extracellular matrix component.

6. The method according to claim 5, wherein the fragmented extracellular matrix component is disposed in a gap among the cells in the tissue construct comprising vascular cells.

7. The method according to claim 5, wherein the fragmented extracellular matrix component is a fragmented collagen component.

8. The method according to claim 5, further comprising:
a step of bringing the cells into contact with the fragmented extracellular matrix component in an aqueous medium before incubation, wherein
the incubating cells comprising at least bovine fat-derived stem cells in the presence of horse serum is a step of incubating the cells brought into contact with the fragmented extracellular matrix component in the presence of horse serum, and
the tissue construct comprising vascular cells is a three-dimensional tissue construct comprising vascular cells.

9. A method for promoting differentiation of fat-derived stem cells, comprising incubating cells comprising at least bovine fat-derived stem cells in a culture medium comprising horse serum in an amount of 5 to 20% of the culture medium,
wherein the incubating is performed for 144 hours or more.

* * * * *